(12) United States Patent
Ashcroft

(10) Patent No.: US 8,997,682 B1
(45) Date of Patent: Apr. 7, 2015

(54) MOISTURE INDICATOR FOR POTTED PLANT SOIL

(76) Inventor: Thomas William David Ashcroft, Granby (CA)

( * ) Notice: Subject to any disclaimer, the term of this patent is extended or adjusted under 35 U.S.C. 154(b) by 11 days.

(21) Appl. No.: 13/600,156

(22) Filed: Aug. 30, 2012

Related U.S. Application Data

(60) Provisional application No. 61/529,604, filed on Aug. 31, 2011.

(51) Int. Cl.
*G01N 21/29* (2006.01)
*A01G 25/16* (2006.01)

(52) U.S. Cl.
CPC .............. *G01N 21/29* (2013.01); *A01G 25/167* (2013.01)

(58) Field of Classification Search
CPC ..... A01G 25/16; A01G 25/167; G01K 11/12; G01N 21/29; G01N 31/22; G01N 31/222; G01N 33/24; G01N 33/246
USPC ......... 73/73, 76; 116/200, 206, 216; 252/963; 436/39, 164–172
See application file for complete search history.

(56) References Cited

U.S. PATENT DOCUMENTS

| | | |
|---|---|---|
| 3,702,755 A | 11/1972 | Palmer |
| 3,881,873 A | 5/1975 | Klowden |
| 3,951,098 A | 4/1976 | Meyers |
| 4,020,785 A | 5/1977 | Palmer |
| 4,063,452 A | 12/1977 | Bradshaw |
| 4,130,012 A | 12/1978 | Lockerby et al. |
| 4,150,570 A | 4/1979 | Fuller |
| 4,184,445 A | 1/1980 | Burrows |
| 4,201,080 A | 5/1980 | Slepak et al. |
| 4,382,380 A | 5/1983 | Martin |
| 4,480,465 A | 11/1984 | Chase |
| 6,058,647 A | 5/2000 | Emalfarb |
| 6,198,398 B1 | 3/2001 | Velasquez |
| 6,202,479 B1 | 3/2001 | Frybarger |
| 6,460,480 B1 | 10/2002 | Schlosser et al. |
| 6,766,762 B2 | 7/2004 | Jenkinson et al. |
| 7,271,729 B2 | 9/2007 | Rice |
| 2010/0012017 A1 | 1/2010 | Miller |

*Primary Examiner* — Laura Martin
*Assistant Examiner* — Irving A Campbell
(74) *Attorney, Agent, or Firm* — Thomas G. Ference

(57) ABSTRACT

The patent application is directed to a moisture indicator that reversibly changes between two different colors depending on whether the moisture indicator is in a wet state or in a dry state. The moisture indicator is used to provide visual information about dryness/wetness of a substrate such as plant soil. The moisture indicator comprises a porous body member having a moisture indicating color and a moisture indicating material over the moisture indicating color. Water passed through the porous material activates the moisture indicating material from a dry opaque state to a transparent clear state. In the transparent clear state, the moisture indicating material reveals the moisture indicating color.

15 Claims, 4 Drawing Sheets

MOISTURE INDICATOR FOR POTTED PLANT SOIL

RELATED APPLICATIONS

This application claims the benefit of priority of U.S. Provisional Patent Application No. 61/529,604, filed Aug. 31, 2011 entitled "Moisture Indicator, Method for Preparing the Same and Method of Use", which is incorporated herein by reference.

FIELD

The patent application generally relates to a moisture indicator that reversibly changes color depending on whether it is in a wet state or in a dry state. The patent application also relates to a method for preparing the same and a use of said moisture indicator to provide visual information about the dryness/wetness of a substrate such as a soil, especially soil in a plant pot.

BACKGROUND

It is known in the art that some chemical compounds reversibly change color when in contact with water. An example of such a chemical compound is cobalt chloride which is blue in its anhydrous state (i.e., $CoCl_2$) and pink in its full hydrated state (i.e., $CoCl_2.6H_2O$).

U.S. Pat. No. 3,951,098 (Meyers) relates to a moisture indicator useful for the monitoring of the moisture content of a potting soil of a conventional house plant. More particularly, this indicator includes a plastic housing encapsulating an elongated wick extending from a lower point where it is exposed beneath the soil level to an upper point in an indicator chamber formed in the housing. The wick surrounds but does not touch a "signal element" comprising a layer of moisture-sensitive, color changeable substance (e.g., cobalt chloride), to carry moisture to the vicinity of the "signal element". The substance changes color in response to predetermined gains (or losses) in moisture content.

U.S. Pat. No. 4,184,445 (Burrows) relates to a moisture indicator for use in determining the wet-dry cycle of soil surrounding cultivated plants. It comprises an upper chamber and lower chamber with an interconnecting passageway across which an absorbent supporting material (e.g., blotting paper) impregnated with a moisture sensitive indicator composition (e.g., cobalt chloride) is positioned. The lower chamber has a bottom opening which upon insertion into the soil results in the relative humidity in the lower chamber being related to the wetness of the soil. The upper chamber is partially transparent and may optionally be vented to the outer atmosphere.

Existing cobalt salts are susceptible to being washed out into the surrounding substrate, thereby involving only a short useful life of a moisture indicator containing the same, and also involving contamination of the soil. In this regard it is to be noted that companies using cobalt chloride have released Material Safety Data Sheets (MSDS) describing cobalt chloride as a skin and respiratory irritant. Also, MSDS reports on the carcinogenic properties of cobalt chloride vary; some state that there is no risk while others say that cobalt chloride has caused cancer in laboratory animals. The warning label that comes with cobalt chloride is that any exposure can irritate the lungs and skin and that long term exposure can affect the heart, kidneys, lungs, and thyroid. Protective eyewear, gloves, respirators and ventilation hoods are the recommended protection measures for handling cobalt chloride.

Furthermore, companies using cobalt chloride as the indicator in their indicating Silica Gel are putting their employees and consumers, as well as the environment, at unnecessary risk. British regulations have required that cobalt chloride be handled and disposed of as a hazardous material since 2001. Cobalt chloride, if not properly disposed of, can leach into the ground and water supply, contaminating both.

A non-cobalt chloride, appearance-changing moisture indicator is described in U.S. Pat. No. 6,058,647 (Emalfarb). The indicator has a body made up of a porous material that changes in physical appearance with a change in the amount of moisture retained in the porous material. In the operative state, a first part of the sensor body resides within the growing medium and a second part of the sensor body remains visible to allow a user to ascertain through the appearance of the second part of the sensor the amount of moisture in the growing medium. The moisture content is ascertained by "darkening" of the porous material in the state with more moisture. The shortcoming of this indicator is that differentiating between shades of the same color can be difficult.

As illustrated by the above mentioned prior art documents, color/appearance changing moisture sensitive indicators either require the assembly of multiple parts for supporting a porous absorbing material that is impregnated with a hazardous moisture sensitive indicator substance such cobalt chloride or they incorporate using a porous material that only changes appearance by different levels of darkening of the same color that is difficult to differentiate visually.

Therefore there is a strong need for a substrate moisture indicator that is inexpensive to manufacture, durable, does not require assembly of multiple parts and clearly reveals the dryness/wetness of the substrate. Also, there is a strong need for a substrate moisture indicator that naturally blends with the surrounding environment. Furthermore, there is a strong need for a moisture indicator that has an extended useful life, prevents contamination of the soil and avoids any negative effects on the health of persons using the indicator. The present patent application puts forth a moisture indicator that meets these aforesaid needs.

SUMMARY

One aspect of the present patent application is directed to a moisture indicator for indicating the water content of a substrate, especially potted plant soil, comprising a body member. The body member is made of at least a porous material having reversible water absorption properties; provided with a moisture indicating surface for positioning above the substrate; provided with a moisture indicating color; and provided with a water transfer surface for contact with the substrate and allowing reversible water migration by capillary action through the porous material between the water transfer surface and the moisture indicating surface. The moisture indicator further includes a moisture indicating material that reversibly changes from opaque when dry to transparent when wet. The moisture indicating surface is at least partially provided with the moisture indicating material and the moisture indicating color is at least partially provided directly beneath the moisture indicating material.

Another aspect of the present patent application is directed to method of preparing a moisture indicator for indicating the water content of a substrate. The method involves providing porous material precursors, colored material and moisture indicating material. The moisture indicating material reversibly changes from opaque when dry to transparent when wet. The method further involves forming the porous material precursors into a body member having reversible water absorption properties with a top surface, a bottom surface and side surfaces. The method then involves coating at least a portion of one of the surfaces with colored material and then coating at least a portion of the colored material with the moisture indicating material to create a moisture indicating surface that displays moisture level color.

Yet another aspect of the present patent application is directed to method of preparing a moisture indicator for indicating the water content of a substrate. The method involves providing porous material precursors, colored material and moisture indicating material. The moisture indicating material reversibly changes from opaque when dry to transparent when wet. The method further involves creating a mixture of the colored material with said porous material precursors and forming the mixture into a body member having reversible water absorption properties with a top surface, a bottom surface and side surfaces. The method then involves coating at least a portion of one of the surfaces with the moisture indicating material to create a moisture indicating surface that displays moisture level color.

BRIEF DESCRIPTION OF DRAWINGS

The foregoing and other aspects and advantages presented in this patent application will be apparent from the following detailed description, as illustrated in the accompanying drawings, in which:

FIG. 2a is a top schematic view of the moisture indicator in FIG. 1a;

DETAILED DESCRIPTION

Figure 1A:
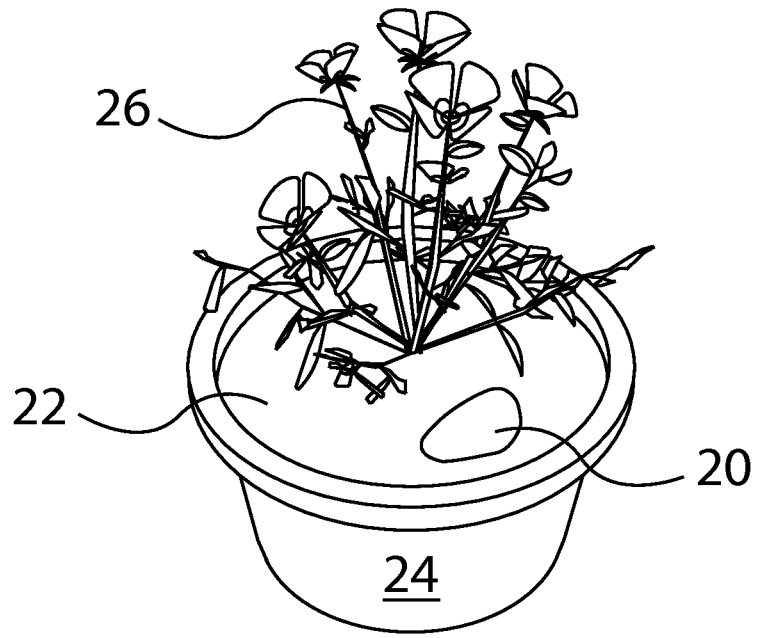
FIG. 1a is a schematic representation of a moisture indicator according to the present patent application, the schematic depicts the moisture indicator pressed into the soil of a potted plant and displaying a moisture level color that indicates that the soil is dry.
Figure 1B:
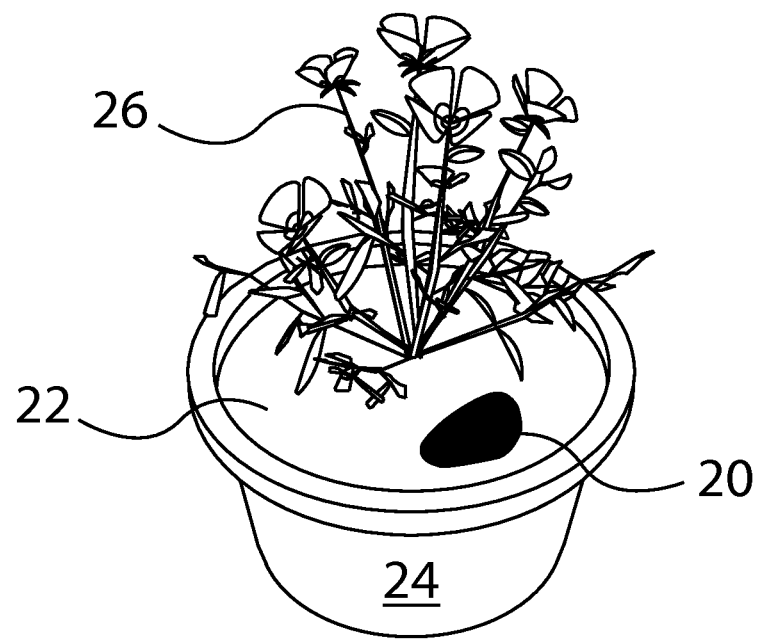
FIG. 1b is a schematic representation of the same moisture indicator as depicted in FIG. 1a, the moisture indicator displaying a moisture level color that indicates the soil is wet.
Figure 2A:
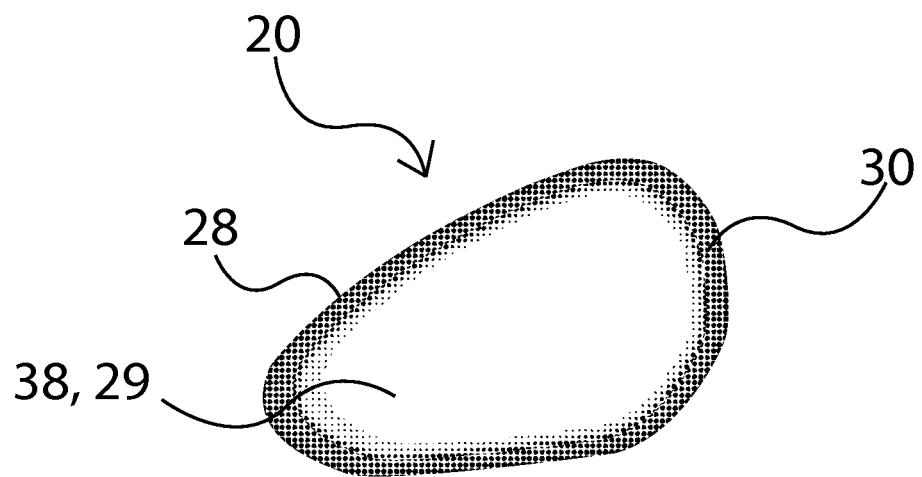
Figure 2B:
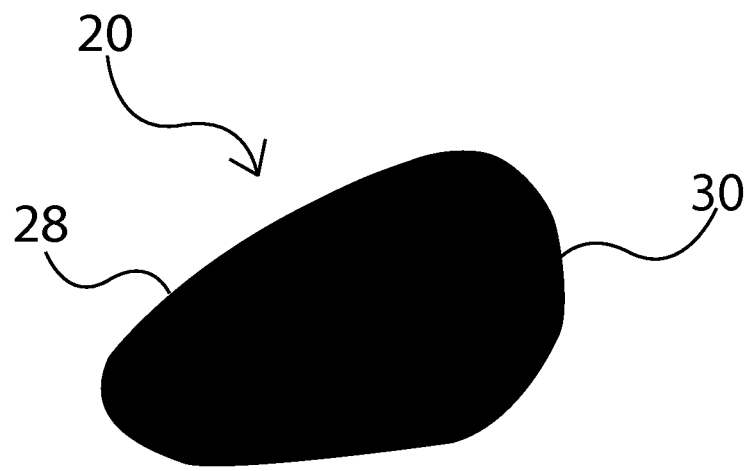
FIG. 2b is a top schematic view of the moisture indicator in FIG. 1b.

FIGS. 1a-4b illustrate the structure and use of a moisture indicator 20. Moisture indicator 20 is for providing visual information to a user about the dryness/wetness of a substrate 22 such as a soil, especially soil in a pot 24 containing a plant 26. Moisture indicator 20 comprises a body member 30 which is made of at least a porous material 32 having reversible water absorption properties. Body member 30 is provided with a moisture indicating surface 34 that is for positioning above substrate 22. Body member 30 is further provided with a moisture indicating color 28, a color that indicates moisture is present. Body member 30 also is provided with a water transfer surface 36 for contact with substrate 22. Water transfer surface 36 allows reversible water migration across the water transfer surface between substrate 22 and porous material 32. Water transfer surface 36 also allows for reversible water migration by capillary action through porous material 32 between the water transfer surface and moisture indicating surface 34. Moisture indicator 20 further comprises a moisture indicating material 38 that reversibly changes from opaque when dry to transparent when wet. Moisture indicating surface 34 is at least partially provided with moisture indicating material 38. Moisture indicating material color 28 is at least partially provided directly beneath moisture indicating material 38.

Body member 30 has as top surface, a bottom surface and side surfaces. Body member 30 is constructed from porous material 32 that has reversible water absorbing properties similar to that of substrate 22, e.g. soil. By having similar reversible water absorbing properties similar to substrate 22, moisture indicator 20 can better represent the water content of the substrate. Porous material 32 needs to be hydrophilic and have an appropriate pore size to transfer water by capillary action. A preferred porous material 32 that exhibits these properties is a porous ceramic such as plaster, clay or gesso. These materials act similar to soil and therefore provide for accurate reading of the moisture content when substrate 22 is plant soil. Discoloration problems and permanent staining of moisture indicator 20 can occur from dissolved chemicals from the soil if the appropriate porous material 32 is not chosen for body member 30. Porous ceramics are less susceptible to staining due to their general chemical inertness. Porous ceramics also provides for a durable moisture indicator 20 that will not deform or break easily. Other alternative porous materials that absorb and retain water are lava rock, soil composites, litmus stone, zeolite, concrete mixes, porous plastic composites, absorbent polymers or super absorbent polymers, foamed plastic, phenolic foam formulations, etc.

Moisture indicator 20 is preferably a stone-shaped body member so that the moisture indicator naturally blends with the surrounding environment. Body member 30 has a thickness defined between water transfer surface 36 and moisture indicating surface 34. Body member 30 also has a minimum width defining moisture indicating surface 34. The minimum width should be greater than the thickness to produce a flat object with a minimum diameter of the area being greater than the thickness. The thickness of body member 30 cannot be too thin or the body will dry quickly and not represent the moisture content of substrate 22. Similarly, the thickness of body member 30 of body member cannot be too thick or it will take too long for water to transfer by capillary action and thereby not represent the moisture content of substrate 22. It is critical to have the thickness of porous material 32 greater than ⅛-inch and less than 1¼ inch.

Moisture indicating surface 34 is preferably defined as substantially the whole top surface of body member 30 to provide a maximum viewable area to the user. However, moisture indicating surface 34 may be some smaller area of the top surface. Moisture indicating surface 34 is provided with moisture indicating material 38 at least partially, but preferably over substantially the entire moisture indicating surface, FIGS. 3a and 4a. Moisture indicating material 38 may alternatively be provided to all surfaces of body member 30, FIGS. 3b and 4b. Moisture indicating material 38 may be a reversible hydrochromic ink such as Hydro-Chromic White manufactured by Matsui International Company, Inc. This product changes repeatedly from white to transparent when wetted with water and changes back to the original white when dried. It consists of a mixture of acrylic acid ester copolymer emulsion and white pigment. Further, when a coloring agent, such as for example Neo Color (coloring pigment paste) is compounded with the binder, it is reversibly changed from colored opaque to colored transparent with water. The critical thickness of the hydrochromic ink that is required is from 0.005 to 0.018-inches thick. If the ink layer is too thin then moisture indicating color 28 is visible. If the ink is too thick, then the color change does not occur and moisture indicating surface 34 remains opaque.

Moisture indicating color 28 is provided at least partially under, but preferably under substantially all of the moisture indicating material 38. Moisture indicating color 28 may be provided as a layer of material between moisture indicating material 38 and porous material 32, FIGS. 3a and 3b. In one embodiment, moisture indicating color is applied as a coating of colored material, the colored material being a porous colored material. Examples of colored material are food dyes, porous oil based paints, pottery dye and water-based paints. Alternatively in another embodiment, moisture indicating color 28 may be incorporated into porous material 32, FIGS. 4a and 4b. Examples of some colored materials that may be incorporated into porous material 32 are pottery dye and pigments.

Figure 3A:
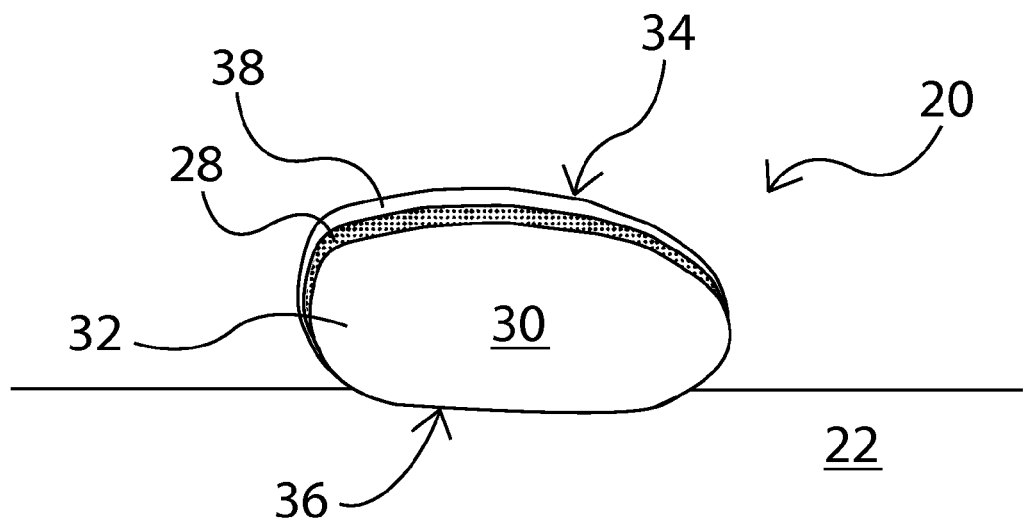
FIG. 3a is a side sectional view of one embodiment for the structure of the moisture indicator shown in either of FIGS. 1a and 1b.
Figure 3B:
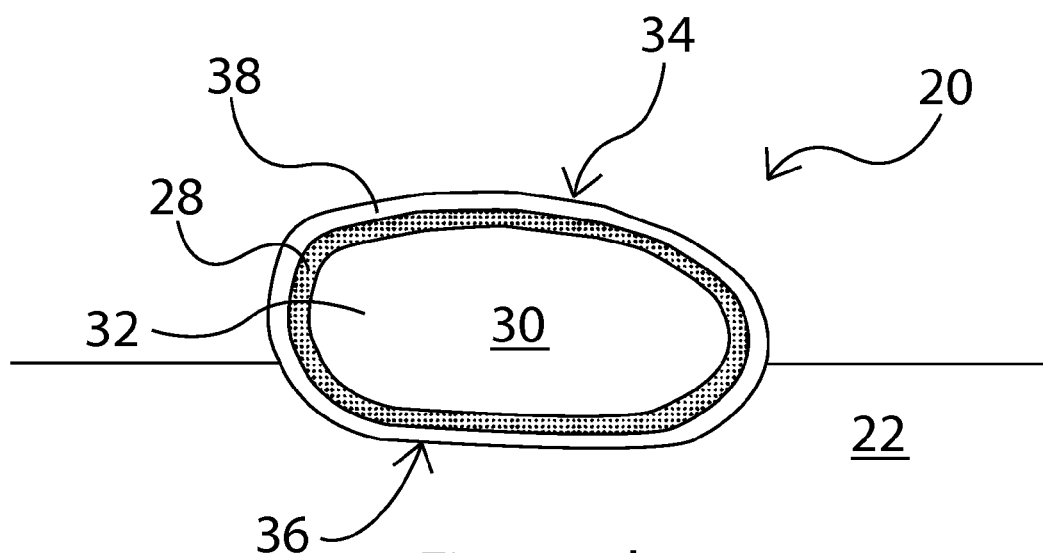
FIG. 3b is a side sectional view of another embodiment for the structure of the moisture indicator shown in either of FIGS. 1a and 1b.

In one embodiment, FIGS. 3a and 3b, the method of preparing moisture indicator 20 for indicating the water content of substrate 22 comprises providing porous material precursors, colored material and moisture indicating material 38. The moisture indicating material 38 reversibly changes from opaque when dry to transparent when wet. The porous material precursors are first formed into body member 30 that has reversible water absorption properties. Porous precursors for plasters and clay include fine ceramic powders, water and other optional aggregates. The water reacts with the ceramic powders to form porous material 32. The result is a body member 30 that has a top surface, bottom surface and side surfaces. A coating of colored material is provided to at least a portion of one surface, FIG. 3a. Finally a coating of moisture indicating material 38 is applied to at least a portion of the colored material. The portion of body member 30 covered by colored material and moisture indicating material 38 creates a moisture indicating surface to display moisture level colors. Alternatively the top surface, bottom surface and side surfaces may all be coated with both colored material and moisture indicating material 38, FIG. 3b.

Figure 4A:
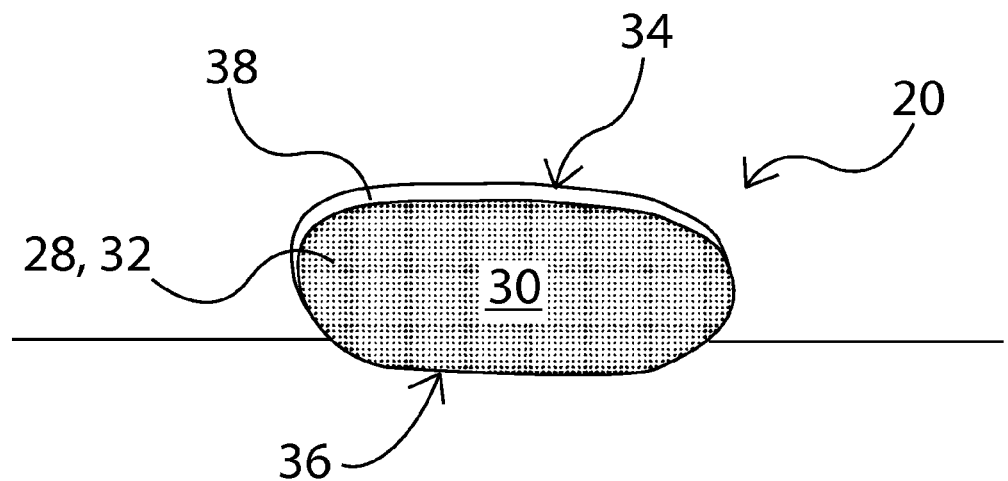
FIG. 4a is a side sectional view of another embodiment for the structure of the moisture indicator shown in either of FIGS. 1a and 1b.
Figure 4B:
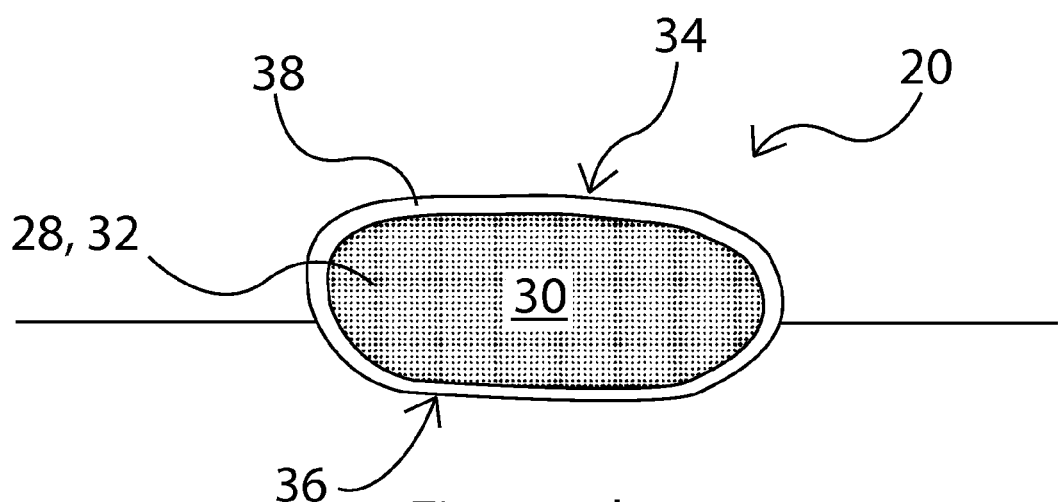
FIG. 4b is a side sectional view of another embodiment for the structure of the moisture indicator shown in either of FIGS. 1a and 1b.

In one embodiment, FIGS. 4a and 4b, the method of preparing moisture indicator 20 for indicating the water content of substrate 22 comprises providing porous material precursors, colored material and moisture indicating material 38. The moisture indicating material 38 reversibly changes from opaque when dry to transparent when wet. A colored material such as a pigment or dye is first mixed with the porous material precursors. The porous material precursors with colored material are then formed into body member 30 that has reversible water absorption properties. Porous precursors for plasters and clay include fine ceramic powders, water and other optional aggregates. The water reacts with the ceramic powders to form porous material 32. The colored material adds color to the whole body member 30. The result is a body member 30 that has a top surface, bottom surface and side surfaces. A coating of moisture indicating material 38 is applied to at least a portion of the colored material, FIG. 4a. The portion of body member 30 covered by moisture indicating material 38 creates a moisture indicating surface to display moisture level color. Alternatively the top surface, bottom surface and side surfaces may all be coated with moisture indicating material 38, FIG. 4b.

Moisture indicator 20 functions as follows. Water transfer surface 36 of moisture indicator 20 is pressed into substrate 22 to create intimate contact with the substrate. Once intimate contact has been created with substrate 22 any water from the substrate passes across water transfer surface 36 and fills the pores in porous material 32. Water continues to migrate by capillary action through the pores and reaches moisture indicating material 38 at moisture indicating surface 34, thereby wetting the moisture indicating material. In the dry state, with no water in moisture indicating material 38, the moisture indicating material is opaque and the user cannot see the color of moisture indicating color 28. The user instead only sees the color of moisture indicating material 38 (dry indicating color 29). However when in the wet state, moisture indicating material 38 is wetted and the moisture indicating material becomes transparent allowing the user to see the color of moisture indicating color 28 beneath the moisture indicating material. The moisture indicating color may also darken in the presence of water. This reversible action that results from water going into and out of the moisture indicating material 38 creates two totally different colors visible to the user between the wet and dry state, see FIG. 2a and 2b. The reversible water absorption properties of all materials allows moisture indicator 20 to reversibly change between the two different colors in response to the moisture content in substrate 22. The reversible color change is repeatable for thousands of times as all materials do not dissolve to any significant amount in water.

A moisture indicator 20 was prepared according to the following technique. First, a slurry was prepared by mixing 70-parts of pottery plaster with 100-parts of water. The slurry was inserted and pressed into a mold to form a body member 30 having a stone-like shape. Pressure applied to the slurry was just sufficient to force it to fill the mold, and if necessary, to reduce/eliminate air bubbles in the molded slurry. A coating of a colored material having water absorption properties was applied to the top surface of the body member. To do so, body member 30 was sprayed with blue paint. The paint used provides a thin porous layer that does not seal the surface from water penetrating it. The painted body member was allowed to dry for a few minutes at room temperature. The colored material was then provided with the moisture indicating material, hydrochromic white. Body member 30 previously coated with blue paint was sprayed with the hydrochromic formulation in a thickness of 0.005 to 0.0018 inches thick. Of course, any other application methods, including other painting methods, can be used. Moisture indicator 20 was then allowed to dry for a few minutes at room temperature.

The stone-like shape is an organic form of approximately 25×25×10 mm. Of course, size of the article may vary within large limits. The size can range anywhere from about ⅛ that size, to 3 times this size. The flattened geometry is particularly preferred to expose as much surface area at the top and bottom of moisture indicator 20. Indeed, a short cylinder, disk, or any other shape that is wider than it is tall will work just as effectively. A particularly preferred specific size is chosen to a) be effective in indication, b) be user friendly to handle and hold, c) be small enough to be unobtrusive in a pot, but large enough to notice when indicating.

While several embodiments of the invention, together with modifications thereof, have been described in detail herein and illustrated in the accompanying drawings; it will be evident that variations in the structure, fabrication and use of the moisture indicator are possible without departing from the scope of the invention. Nothing in the above specification is intended to limit the invention more narrowly than the appended claims. The examples given are intended only to be illustrative rather than exclusive.

What is claimed is:

1. A moisture indicator for indicating the water content of a substrate, comprising:
   a) a body member which is:
      i) made of at least a porous material having reversible water absorption properties,
      ii) provided with a moisture indicating surface for positioning above the substrate, said moisture indicating surface displaying a moisture level color,
      iii) provided with a moisture indicating color,
      iv) provided with a water transfer surface for contact with the substrate and allowing reversible water migration by capillary action through said porous material between the substrate and said moisture indicating surface;
   b) a moisture indicating material that reversibly changes from opaque when dry to transparent when wet; and
   c) wherein said moisture indicating surface is at least partly provided with said moisture indicating material on said porous material, and wherein said moisture indicating color is at least partially provided directly beneath said moisture indicating material.

2. A moisture indicator as recited in claim 1, wherein said body member has a thickness between said water transfer surface and said moisture indicating surface, wherein said moisture indicating surface has a minimum width, wherein said minimum width is greater than said thickness.

3. A moisture indicator as recited in claim 2, wherein said thickness is greater than 1/8-inch and less than 1 1/4 inch.

4. A moisture indicator as recited in claim 1, wherein said body member has a top surface, wherein said moisture indicating surface is substantially said whole top surface.

5. A moisture indicator as recited in claim 1, wherein said body member has a top surface, wherein said moisture indicating material is provided at substantially all of said top surface.

6. A moisture indicator as recited in claim 1, wherein said moisture indicating color is provided under substantially all of said moisture indicating material.

7. A moisture indicator as recited in claim 1, wherein said porous material is a porous ceramic.

8. A moisture indicator as recited in claim 7, wherein said porous ceramic is at least one from the group including plaster and clay.

9. A moisture indicator as recited in claim 1, where in said moisture indicating color darkens in the presence of water.

10. A moisture indicator as recited in claim 1, wherein said moisture indicating color is incorporated into said porous material.

11. A moisture indicator as recited in claim 1, wherein said moisture indicating material is a reversible hydrochromic ink.

12. A moisture indicator as recited in claim 11, wherein said hydrochromic ink is from 0.005-0.018 inches thick.

13. A moisture indicator for indicating the water content of a substrate, comprising:
   a) a body member which is:
      i) made of at least a porous material having reversible water absorption properties,
      ii) provided with a moisture indicating surface for positioning above the substrate, said moisture indicating surface displaying a moisture level color,
      iii) provided with a moisture indicating color,
      iv) provided with a water transfer surface for contact with the substrate and allowing reversible water migration by capillary action through said porous material between the substrate and said moisture indicating surface;
   b) a moisture indicating material that reversibly changes from opaque when dry to transparent when wet; and
   c) wherein said moisture indicating surface is at least partly provided with said moisture indicating material, wherein said moisture indicating color is at least partially provided directly beneath said moisture indicating material, wherein said moisture indicating material is provided at both said water transfer surface and said moisture indicating surface, wherein said moisture indicating color is provided between said porous material and said moisture indicating material at both said water transfer surface and said moisture indicating surface.

14. A moisture indicator as recited in claim 13, wherein said porous material is a porous ceramic.

15. A moisture indicator as recited in claim 13, wherein said moisture indicating material is a reversible hydrochromic ink.

* * * * *